(12) United States Patent
Kuyava et al.

(10) Patent No.: US 7,914,439 B2
(45) Date of Patent: *Mar. 29, 2011

(54) IMPLANTABLE PENILE PROSTHESIS PUMP

(75) Inventors: Charles C. Kuyava, Eden Prairie, MN (US); Gary A. Rocheleau, Maple Grove, MN (US); Greg J. Henkel, Chanhassen, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/617,764

(22) Filed: Nov. 13, 2009

(65) Prior Publication Data

US 2010/0056859 A1    Mar. 4, 2010

Related U.S. Application Data

(63) Continuation of application No. 11/305,672, filed on Dec. 16, 2005, now Pat. No. 7,637,861.

(60) Provisional application No. 60/637,032, filed on Dec. 17, 2004.

(51) Int. Cl.
*A61F 5/00* (2006.01)
(52) U.S. Cl. .......................................... 600/40
(58) Field of Classification Search .............. 600/29–32, 600/38–41; 623/11.11; 128/843
See application file for complete search history.

(56) References Cited

U.S. PATENT DOCUMENTS

| | | | |
|---|---|---|---|
| 3,954,102 A | 5/1976 | Buuck | |
| 4,222,377 A | 9/1980 | Burton | |
| 4,224,934 A | 9/1980 | Scott et al. | |
| 4,235,227 A | 11/1980 | Yamanaka | |
| 4,267,829 A | 5/1981 | Burton et al. | |
| 4,383,525 A | 5/1983 | Scott et al. | |
| 4,407,278 A | 10/1983 | Burton et al. | |
| 4,412,530 A | 11/1983 | Burton | |
| 4,441,491 A | 4/1984 | Evans, Sr. | |
| 4,566,446 A | 1/1986 | Fogarty | |
| 4,572,168 A | 2/1986 | Fischell | |
| 4,590,927 A | 5/1986 | Porter et al. | |
| 4,596,242 A | 6/1986 | Fischell | |
| 4,602,625 A | 7/1986 | Yachia et al. | |

(Continued)

FOREIGN PATENT DOCUMENTS

DE    25 37 506 A1    3/1977

(Continued)

OTHER PUBLICATIONS

Gregory, John G. et al., The Inflatable Penile Prosthesis: Failure of the Rear Tip Extender in Reducing the Incidence of Cylinder Leakage, The Journal of Urology, vol. 131, pp. 668-669 (Apr. 1984).

(Continued)

*Primary Examiner* — John P Lacyk
(74) *Attorney, Agent, or Firm* — Kimberly K. Baxter; Gregory L. Koeller

(57) ABSTRACT

Pumps for use with inflatable implantable penile prostheses in accordance with the invention include features that can provide for free fluid flow during inflation and deflation modes of the pump. Pumps may also include a bypass chamber that is fluidly connected to the fluid passageway by a bypass input channel and a bypass output channel. The bypass chamber comprises a bypass check valve biased toward a closed position.

1 Claim, 13 Drawing Sheets

U.S. PATENT DOCUMENTS

| | | | |
|---|---|---|---|
| 4,651,721 A | 3/1987 | Mikulich et al. | |
| 4,653,485 A | 3/1987 | Fischell | |
| 4,682,583 A | 7/1987 | Burton et al. | |
| 4,718,410 A | 1/1988 | Hakky | |
| 4,782,826 A | 11/1988 | Fogarty | |
| 4,807,608 A | 2/1989 | Levius | |
| 4,895,139 A | 1/1990 | Hauschild et al. | |
| 5,010,882 A | 4/1991 | Polyak et al. | |
| 5,048,510 A | 9/1991 | Hauschild et al. | |
| 5,062,417 A | 11/1991 | Cowen | |
| 5,112,295 A | 5/1992 | Zinner et al. | |
| 5,114,398 A | 5/1992 | Trick et al. | |
| 5,141,509 A | 8/1992 | Burton et al. | |
| 5,167,611 A | 12/1992 | Cowan | |
| 5,171,272 A | 12/1992 | Levius | |
| 5,250,020 A | 10/1993 | Bley | |
| 5,263,981 A | 11/1993 | Polyak et al. | |
| 5,344,388 A | 9/1994 | Maxwell et al. | |
| 5,704,895 A | 1/1998 | Scott et al. | |
| 5,851,176 A | 12/1998 | Willard | |
| 6,171,233 B1 | 1/2001 | Willard | |
| 6,443,887 B1 | 9/2002 | Derus et al. | |
| 6,533,719 B2 | 3/2003 | Kuyava et al. | |
| 6,558,315 B1 | 5/2003 | Kuyava | |
| 6,723,042 B2 | 4/2004 | Almli et al. | |
| 7,637,861 B2 * | 12/2009 | Kuyava et al. | 600/40 |
| 2002/0033564 A1 | 3/2002 | Koyfman | |
| 2002/0082473 A1 | 6/2002 | Henkel et al. | |
| 2002/0082709 A1 | 6/2002 | Almli et al. | |
| 2002/0091302 A1 | 6/2002 | Kuyava et al. | |
| 2003/0028076 A1 | 2/2003 | Kuyava et al. | |
| 2004/0220447 A1 | 11/2004 | Morningstar | |

FOREIGN PATENT DOCUMENTS

| | | |
|---|---|---|
| EP | 0 397 500 A2 | 11/1990 |
| WO | WO 92/03107 A | 3/1992 |
| WO | WO 02/051339 | 7/2002 |

OTHER PUBLICATIONS

Hellstrom, WJG, Three-Piece Inflatable Penile Prosthesis Components (Surgical Pearls on Reservoirs, Pumps, and Rear-Tip Extenders), Int'l J of Impotence Research, vol. 15, Suppl. 5, pp. S136-138 (2003).

Joseph, David et al., Bilateral Dislocation of Rear Tip Extenders From the Inflatable Penile Prosthesis, The Journal of Urology, vol. 128, pp. 1317-1318 (Dec. 1982).

Kim, Sae-Chul, M.D., Mechanical Reliability of AMS Hydraulic Penile Prostheses, Journal of Korean Medical Science, vol. 10, No. 6, pp. 422-425 (Dec. 1995).

Levine, Laurence A. et al., Mechanical Reliability and Safety of, and Patient Satisfaction With the Ambicor Inflatable Penile Prosthesis: Results of a 2 Center Study, The Journal of Urology, vol. 166, pp. 932-937 (Sep. 2001).

Malloy, Terrance R. et al., Improved Mechanical Survival With Revised Model Inflatable Penile Prosthesis Using Rear-Tip Extenders, The Journal of Urology, vol. 128, pp. 489-491 (Sep. 1982).

Montague, Drogo K., Experience With Semirigid Rod and Inflatable Penile Prosthesis, The Journal of Urology, vol. 129, pp. 967-968 (May 1983).

Mooreville, Michael et al., Implantation of Inflatable Penile Prosthesis in Patients With Severe Corporeal Fibrosis: Introduction of a New Penile Cavernotome, The Journal of Urology, vol. 162, pp. 2054-2057 (Dec. 1999).

Mulcahy, John J., Distal Corporoplasty for Lateral Extrusion of Penile Cylinders, The Journal of Urology, vol. 161, pp. 193-195 (Jan. 1999).

Parulkar, B.G. et al., Revision Surgery for Penile Implants, Int. J. Impotence Res., vol. 6, pp. 17-23 (1994).

Randrup, Eduardo R., M.D., Penile Implant Surgery: Rear Tip Extender That Stays Behind, Urology, vol. XXXIX, No. 1, pp. 667-669 (Jan. 1992).

Stein, Avi et al., Malleable Penile Prosthesis Removal Leaving Behind the Rear Tip Extenders; A Clinical Presentation, Urol. Int., 50, pp. 119-120 (1993).

AMS700™ *Inflatable Penile Prosthesis Product Line, Inservice Script* brochure, American Medical Systems (1992).

*Ultrex/Ultrex Plus* brochure, American Medical Systems, Inc. (1998).

Description of Ultrex Fabric and Yarns (Mar. 30, 2001).

Mentor Alpha I® Inflatable Penile Prosthesis, Surgical Protocol, 15 pages (1998).

Mentor Urology Products, 20 pages (May 1998).

Mentor Alpha I®, The Results are In, 14 pages (Apr. 1997).

Mentor Alpha I® Narrow Base, Simplifying Penile Implant Surgery by Making Difficult Cases More Manageable, 2 pages (Oct. 1996).

Mentor® Acu-Form® Penile Prosthesis, 2 pages (Aug. 1997).

Mentor® Acu-Form® Penile Prosthesis, Malleable Penile Prosthesis, Surgical Protocol, 8 pages (Sep. 1997).

Mulcahy, John J., Another Look At the Role of Penile Prostheses in the Management of Impotence, pp. 169-185 (1997).

* cited by examiner

IMPLANTABLE PENILE PROSTHESIS PUMP

REFERENCE TO RELATED APPLICATIONS

This application is a continuation application of U.S. application Ser. No. 11/305,672, filed Dec. 16, 2005 now U.S. Pat. No. 7,637,861, which claims the benefit of U.S. provisional patent application No. 60/637,032, filed Dec. 17, 2004, entitled "Side Squeeze Momentary Squeeze Pump," the entire disclosures of which are incorporated herein by reference for all purposes.

TECHNICAL FIELD

The invention relates to systems for treating erectile dysfunction and other urological disorders. In particular, the invention relates to pumps for use with inflatable implantable penile prostheses.

BACKGROUND

One common treatment for male erectile dysfunction is the implantation of a penile prosthesis. Such a prosthesis typically includes a pair of inflatable cylinders, which are fluidly connected to a reservoir via a pump and valve assembly. The two cylinders are normally implanted into the corpus cavernosae of the patient and the reservoir is typically implanted into the patient's abdomen. The pump assembly is implanted in the scrotum.

During use, the patient actuates the pump and fluid is transferred from the reservoir through the pump and into the cylinders. This results in the inflation of the cylinders and thereby produces the desired penis rigidity for a normal erection. Then, when the patient desires to deflate the cylinders, a valve assembly within the pump is actuated in a manner such that the fluid in the cylinders is released back into the reservoir. This deflation then returns the penis to a flaccid state.

Presently, the pump and valve assembly used in such implantable prostheses share certain similar characteristics. For example, they include fluid pathways allowing the flow of fluid to and from the reservoir, as well as to and from the cylinders. In some designs this fluid flow is controlled by one or more poppet valves positioned in such fluid pathways within the housing of the assembly.

A compressible pump bulb is also attached to the housing and is in fluid communication with the various fluid pathways. In order to inflate the cylinders, the compressible pump bulb is actuated by the patient, thereby urging fluid in the bulb past the poppet valves into the cylinders. In order to deflate the cylinders, the valve housing is grasped and squeezed, through the patient's tissue, causing the various poppet valves to unseat and allow fluid to flow back to the reservoir.

SUMMARY

Pumps for use with inflatable penile prostheses in accordance with the invention can be designed to include advantageous features such as the ability to functionally arrange valve components in a compact manner and different alignment between functional valve components.

In one aspect of the invention, a pump that provides a feature that allows a free path for fluid flow under certain conditions is provided. The pump preferably comprises a pump housing, first and second fluid ports, and a pump bulb. The pump housing comprises a fluid passageway. The first and second fluid ports are in fluid communication with the fluid passageway and are operatively connectable to a fluid reservoir and at least one inflatable penile prosthesis, respectively. The pump bulb is in fluid communication with the fluid passageway and can be operated to transfer fluid between the first and second fluid ports through the fluid passageway. The pump comprises a poppet positioned within the fluid passageway. The poppet includes an extending portion extending away from a body portion of the poppet. The extending portion has a sealing surface biased toward a valve seat within the fluid passageway. The pump includes a flange extending from a surface of the fluid passageway and toward the interior of the fluid passageway and spaced from the valve seat within the fluid passageway. One or more of the flange and the extending portion of the poppet may include one or more protrusions that provide a gap between the flange and extending portion of the poppet. In one embodiment of a refill phase of pumping, a fluid path is established between the extending portion of the poppet and the flange when the extending portion of the poppet is in contact with the flange so that fluid can pass from one side of the flange to the other.

In another aspect of the invention, a pump with slidingly engaged poppets is provided. The pump preferably comprises a pump housing, first and second fluid ports, and a pump bulb. The pump housing comprises a fluid passageway. The first and second fluid ports are in fluid communication with the fluid passageway and are operatively connectable to a fluid reservoir and at least one inflatable penile prosthesis, respectively. The pump bulb is in fluid communication with the fluid passageway and can be operated to transfer fluid between the first and second fluid ports through the fluid passageway. The pump includes first and second poppets positioned within the fluid passageway and biased toward first and second valve seats within the fluid passageway, respectively. The first poppet comprises an end slidingly engaged with an end of the second poppet.

In yet another aspect of the invention a pump having a bypass chamber is provided. The pump preferably comprises a pump housing, first and second fluid ports, and a pump bulb. The pump housing comprises a fluid passageway. The first and second fluid ports are in fluid communication with the fluid passageway and are operatively connectable to a fluid reservoir and at least one inflatable penile prosthesis, respectively. The pump bulb is in fluid communication with the fluid passageway and can be operated to transfer fluid between the first and second fluid ports through the fluid passageway. First and second poppets are positioned within the fluid passageway, aligned along a poppet valve axis, and biased toward first and second valve seats within the fluid passageway, respectively. The bypass chamber is fluidly connected by a bypass input channel to the fluid passageway at a first location and fluidly connected by a bypass output channel to the fluid passageway at a second location. The bypass chamber comprises a bypass check valve biased toward a closed position along a check valve axis. The check valve axis is oriented in a non-parallel manner with respect to the valve axis of the first and second poppets.

BRIEF DESCRIPTION OF THE DRAWINGS

The invention will be further explained with reference to the appended Figures, wherein like structure is referred to by like numerals throughout the several views, and wherein.

DETAILED DESCRIPTION

Figure 1:
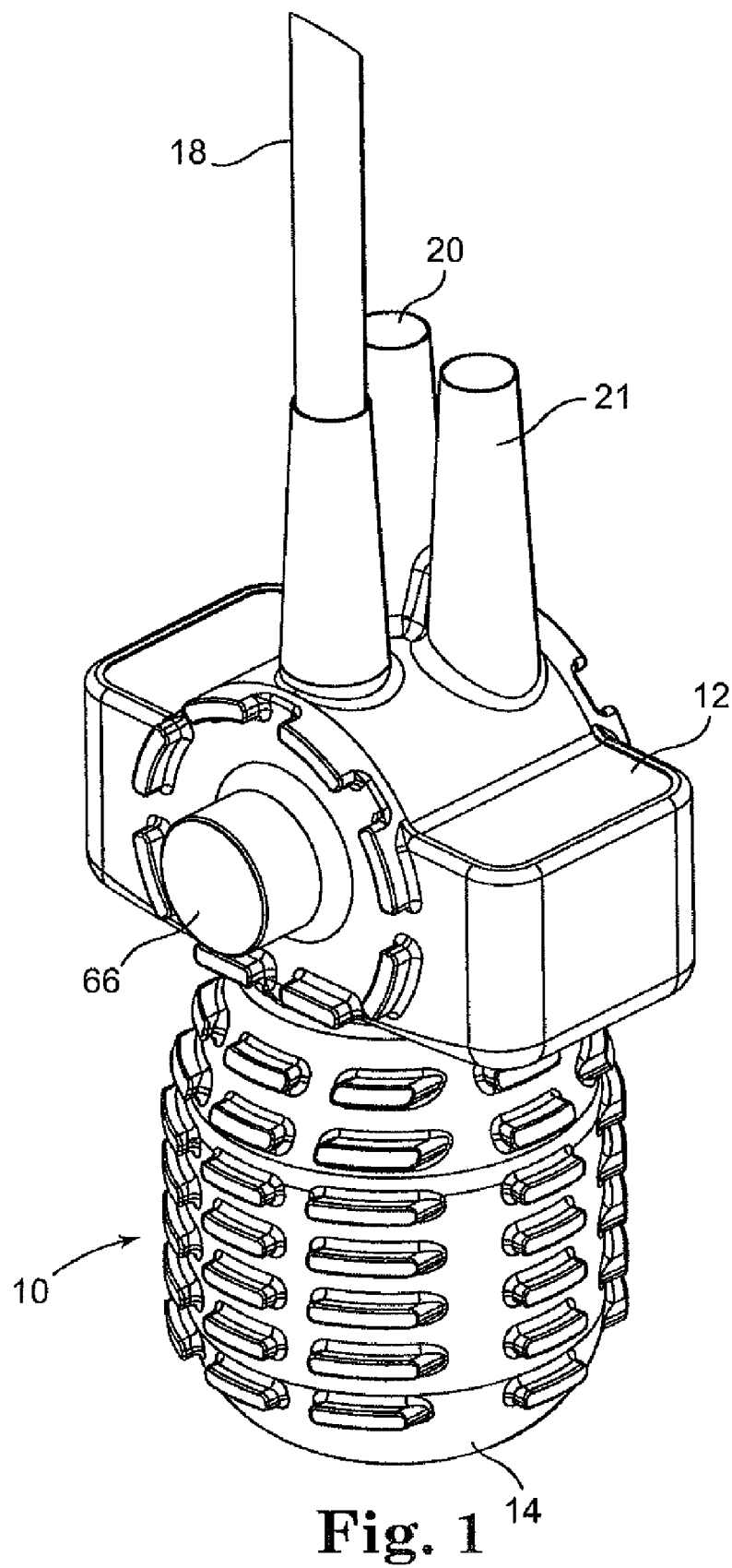
FIG. 1 is a perspective view of a pump assembly that can be used with an inflatable implantable penile prostheses in accordance with the invention.
Figure 2:
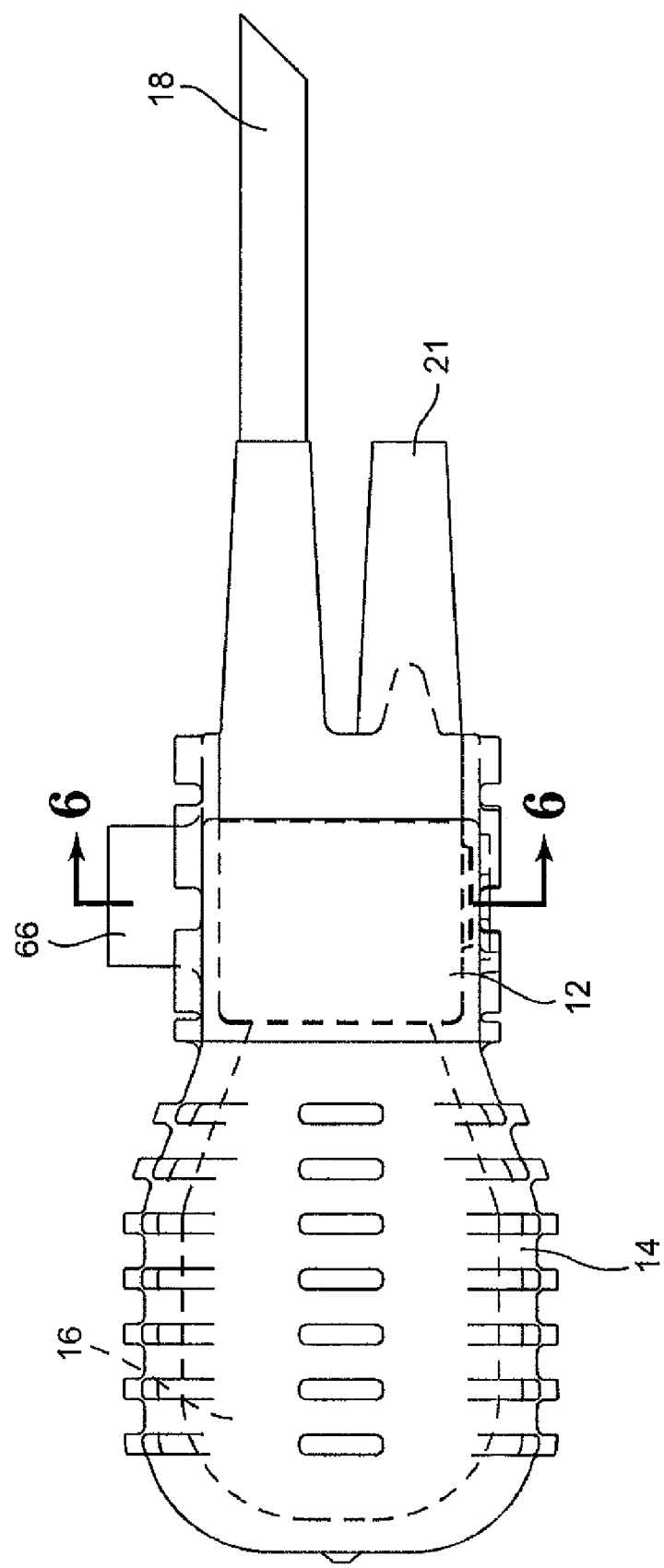
FIG. 2 is a side view of the pump assembly illustrated in FIG. 1.
Figure 3:
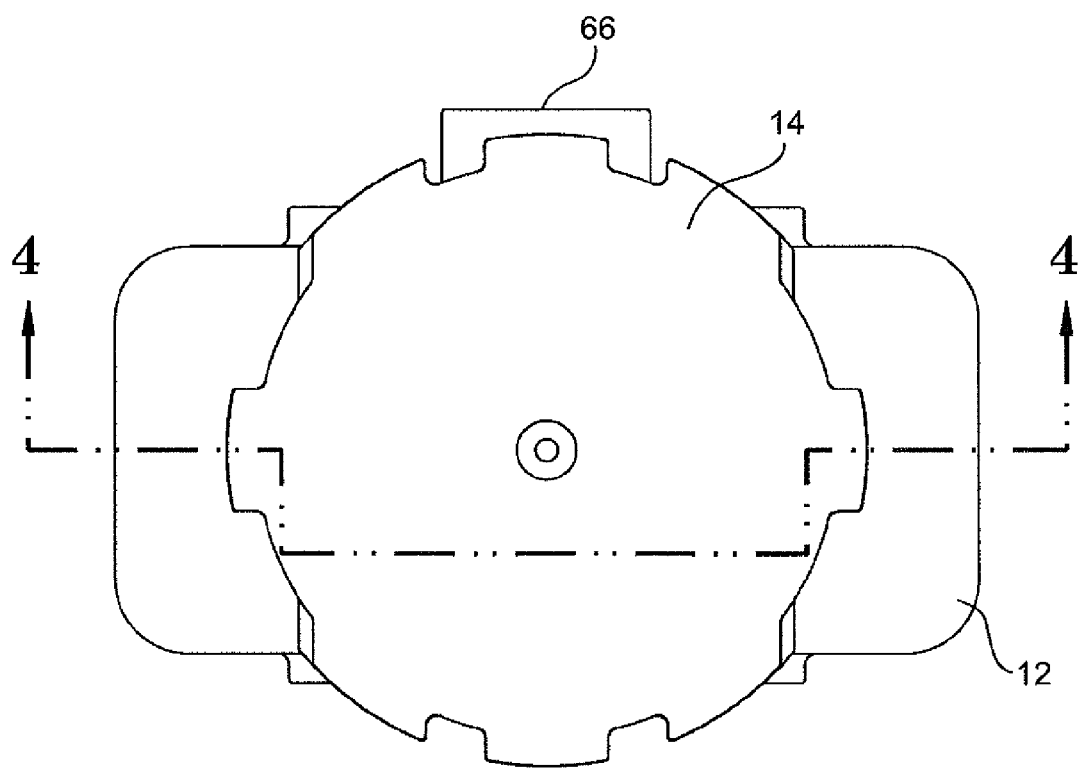
FIG. 3 is bottom view of the pump assembly illustrated in FIG. 1.
Figure 4:
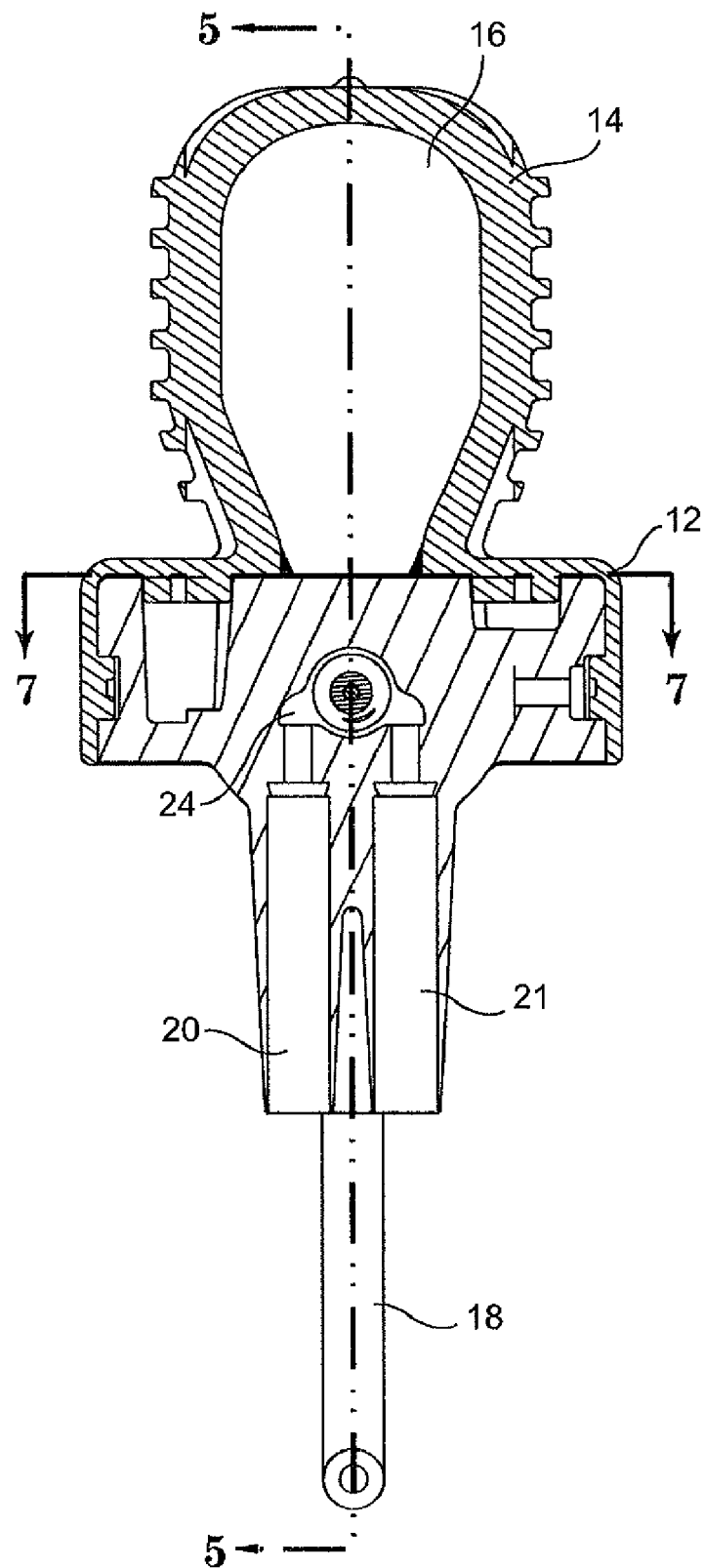
FIG. 4 is a cross-sectional view of the pump assembly illustrated in FIG. 3, taken along the line 4-4.
Figure 5:
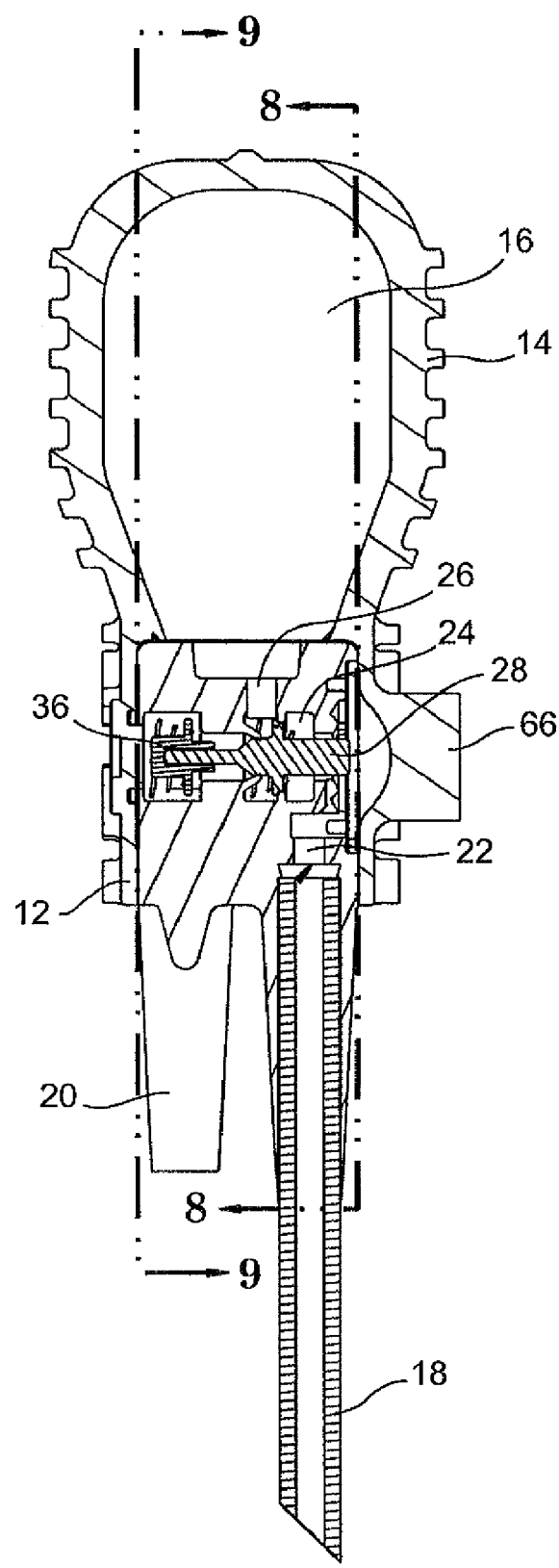
FIG. 5 is a cross-sectional view of the pump assembly illustrated in FIG. 4, taken along the line 5-5.

Referring to FIGS. 1 through 9 and 13, pump assembly 10 for use in an implantable penile prosthesis system is illustrated. In FIGS. 1 through 3, a perspective, side, and bottom view of the pump assembly 10 are shown, respectively. In FIGS. 4 through 9 and 13, various cross-sectional views of the pump assembly 10 are shown to illustrate its various functional aspects and components. In general, when a penile prosthesis system is implanted into a person, a pump assembly, such as pump assembly 10, is positioned within the user's scrotum, two inflatable cylinders are positioned within the user's corpus cavernosae and a reservoir is implanted in the user's abdomen. One or more tubes provide fluid communication between assembly 10 and the cylinders and between assembly 10 and the reservoir. In this embodiment, assembly 10 includes housing or pump body 12 connected to pump bulb 14 having an internal chamber 16. Pump assembly 10 is connected for fluid communication with at least one inflatable cylinder (not shown) by ports 20 and 21, which preferably comprise flexible silicone tubes. Alternatively, pump assembly 10 can be designed with a single port that comprises a single tube that could be fluidly connected directly to pump assembly 10 and branch into multiple tubes that extend to each of the cylinders at some distance from pump assembly 10. Any such tube is preferably relatively flexible for comfort and conformability within a patient, and may have a constant or varying (e.g., tapered) diameter along its length.

Pump assembly 10 is further connected for fluid communication with at least one fluid-filled reservoir (not shown) by at least one reservoir port 18 that preferably comprises a flexible silicone tube as shown. While only one port is used in the embodiment shown in FIG. 1, assembly 10 may include additional ports for connection to one or more reservoirs, or a single port may be fluidly connected to pump assembly 10 with a tube that branches into multiple tubes that connect to one or more reservoirs. In the preferred embodiment, however, port 18 is provided to fluidly connect pump assembly 10 to a single reservoir, which is typically implanted in the abdomen or some other location in the user's body that is spaced from pump assembly 10. Any such tube used with port 18 is preferably made of a relatively flexible material, such as silicone, and is sufficiently long for connecting the reservoir to the pump body when these components are implanted in their desired locations in the body.

Pump assembly 10 of the invention is controllable by the user to move fluid to and from the inflatable cylinders, as desired. Importantly, pump assembly 10 preferably includes features that can eliminate or reduce the possibility of a vacuum lock that can interrupt the inflation process as described in more detail below. Preferably, pump assembly 10 also includes poppets that slidingly engage to provide an alignment feature for such poppets in the pump assembly. In addition, pump assembly 10 is preferably configured so that poppet valve components of pump assembly 10 are provided along a short axis of pump body 12. In this way, a stable platform for the user's fingers to hold onto the pump assembly and squeeze for deflation is provided. Thus, pump assembly 10 provides a reliable controllable device that is easily manipulated by the user to inflate and deflate the cylinders, as desired.

Figure 6:
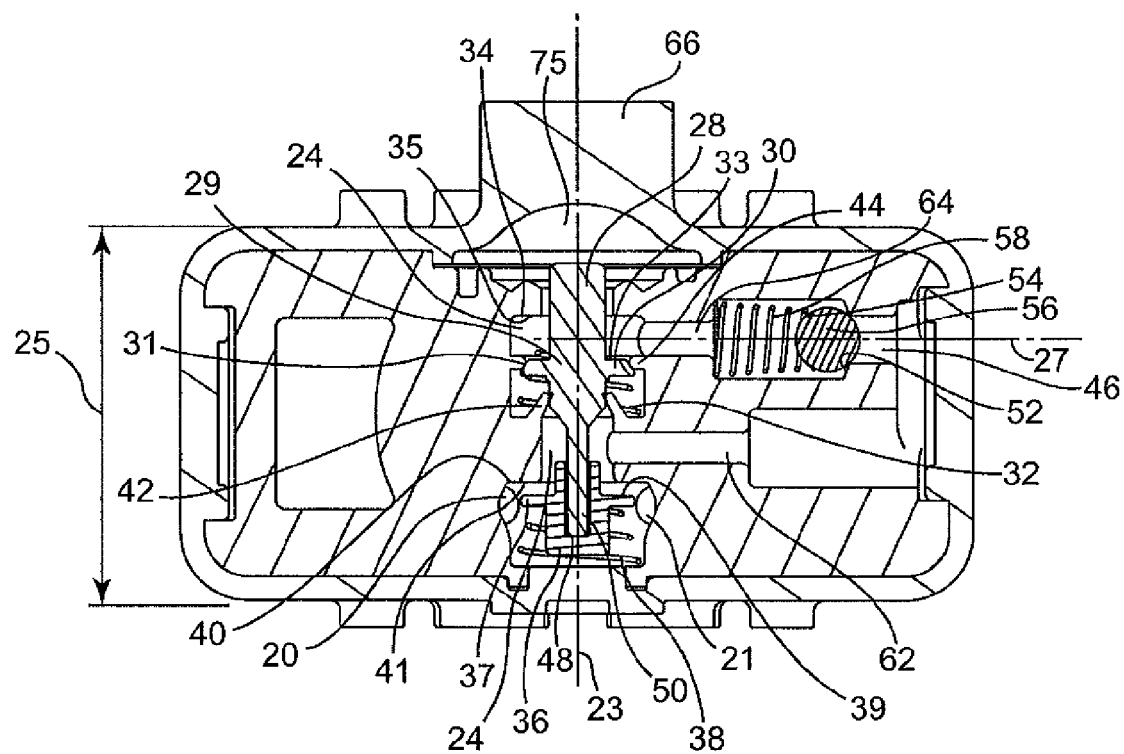
FIG. 6 is a cross-sectional view of the pump assembly illustrated in FIG. 2, taken along the line 6-6.
Figure 7:
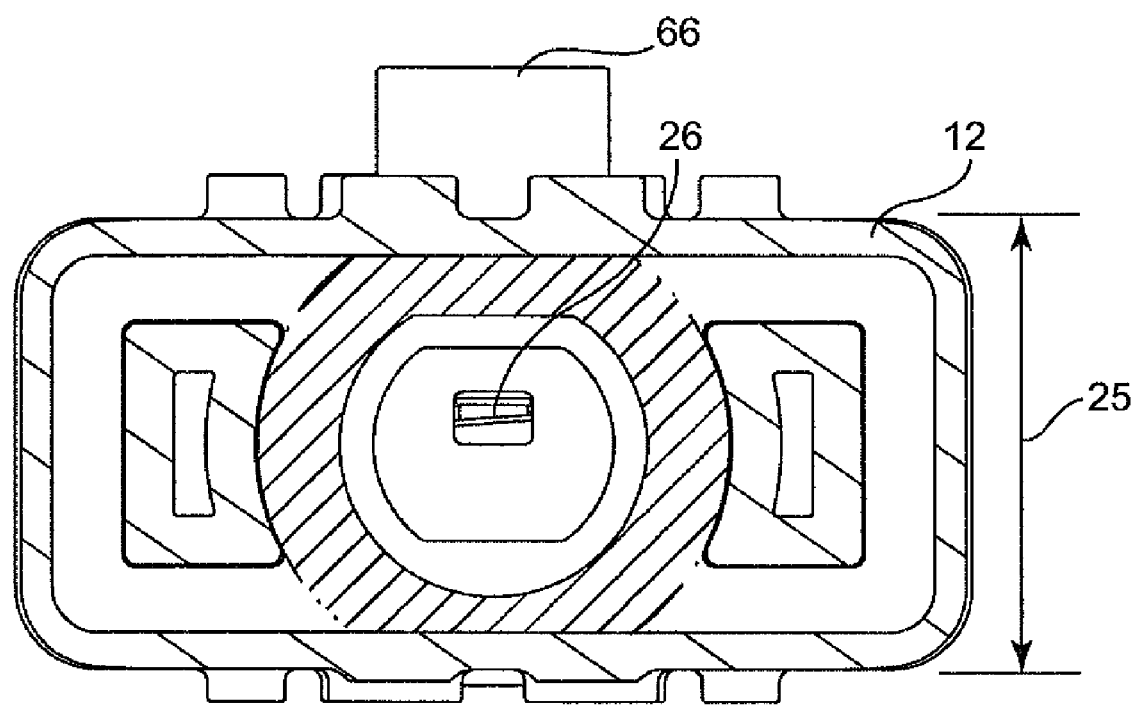
FIG. 7 is a cross-sectional view of the pump assembly illustrated in FIG. 4, taken along the line 7-7.
Figure 8:
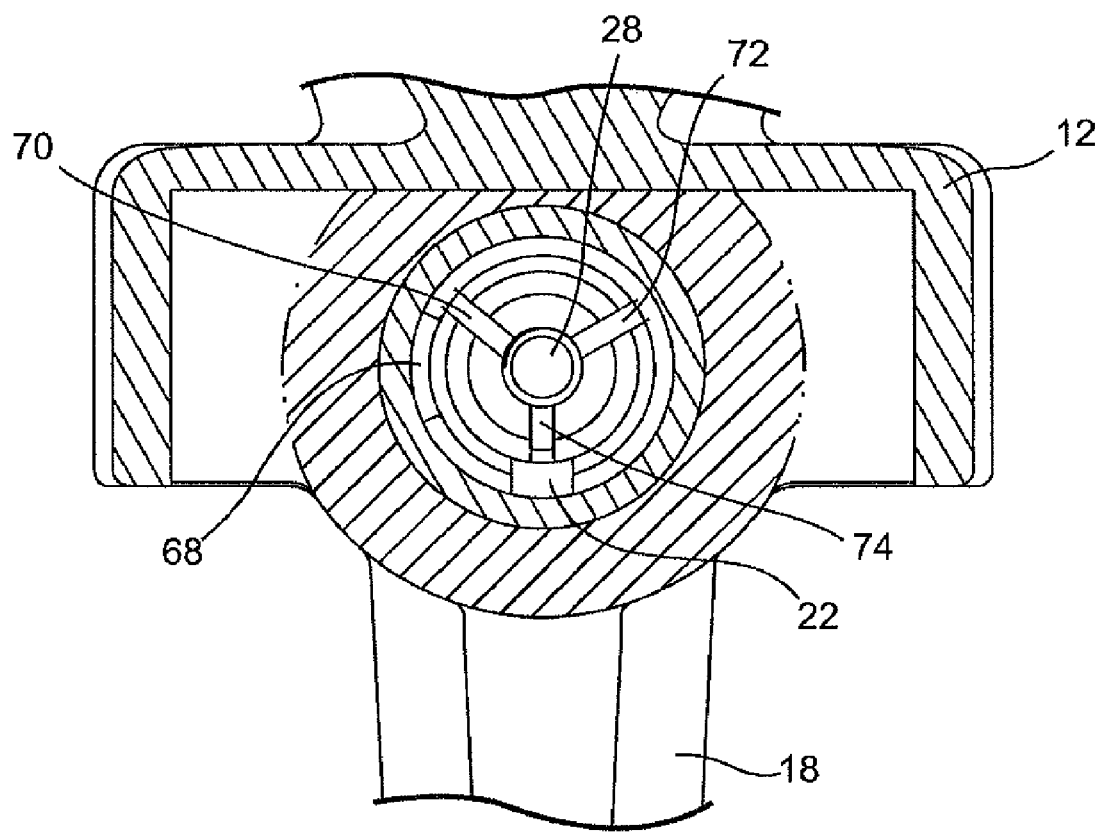
FIG. 8 is a cross-sectional view of the pump assembly illustrated in FIG. 5, taken along the line 8-8.
Figure 9:
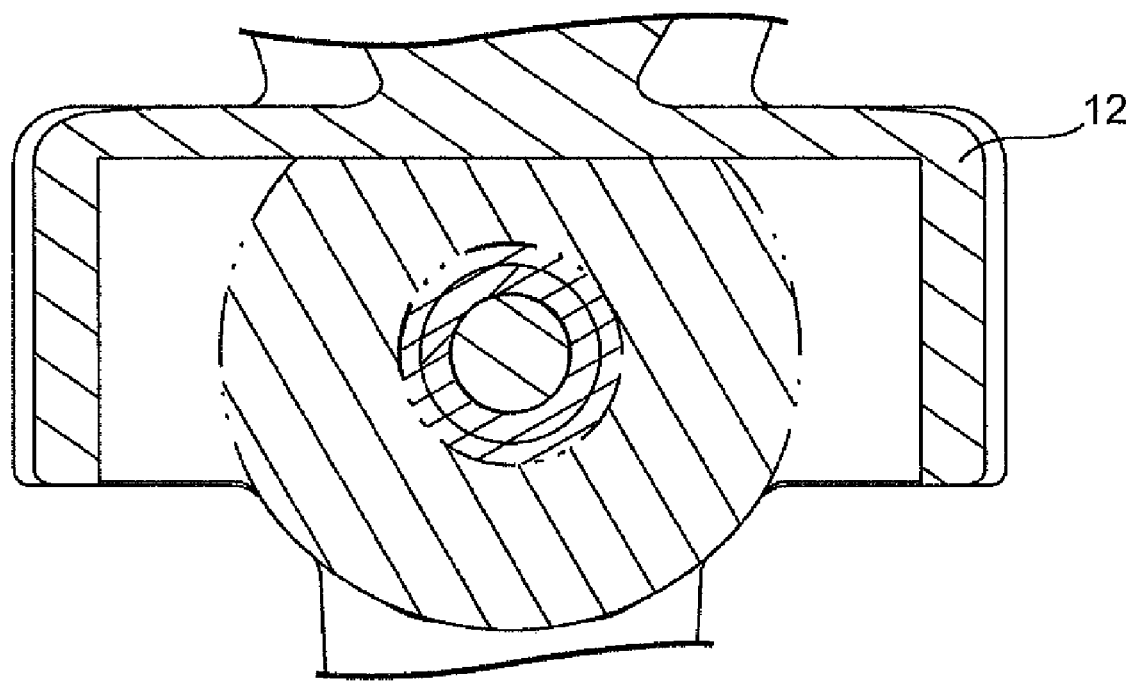
FIG. 9 is a cross-sectional view of the pump assembly illustrated in FIG. 5, taken along the line 9-9.

Pump body 12 preferably comprises a generally flexible device that includes a number of components to provide the desired movement of fluid through its internal chambers. Reservoir port 18 is fluidly connected to transfer chamber 22 within pump body 12. As can be seen best in the section view of FIG. 8, transfer chamber 22 is fluidly connected to annular channel 68 and radial channels 70, 72, and 74. Transfer chamber 22 can also fluidly communicate with ports 20 and 21 through connecting fluid passageway 24 (see FIGS. 4 and 5, for example). Fluid passageway 24 is further connected to internal chamber 16 of pump bulb 14 by connecting channel 26 (see FIG. 5), where the various fluidic connections can be initiated and terminated with the operation of pump assembly 10, as described below. As shown in FIG. 6, for example, fluid passageway 24 is a generally elongated chamber that extends across a portion of width 25 of pump body 12 and provides a passageway through which fluid can flow between the components of pump assembly 10, such as a reservoir, internal chamber 16, fluid bypass chamber 46, and cylinders.

Referring particularly to FIG. 6, fluid passageway 24 includes within its internal area a check valve system that generally includes reservoir poppet 28 and cylinder poppet 36. Reservoir poppet 28 and cylinder poppet 36 are preferably coaxially aligned with each other on a poppet valve axis 23 along the length of passageway 24, with both poppets preferably being centrally positioned within passageway 24. Reservoir poppet 28 has a generally elongated shape and is designed for contact and sealing with various components of the system during its operation. In particular, reservoir poppet 28 includes elongated body 29 that is preferably generally cylindrical, as shown, although it can take any number of shapes that fit within the internal chamber of fluid passageway 24 to provide contact with its surfaces and control the movement of fluid. Reservoir poppet 28 further includes face seal portion 30 that is preferably a ring-like protrusion that extends around the outer perimeter of elongated body 29. As shown, face seal portion 30 is positioned near the center of the length of elongated body 29, although it is possible that portion 30 is closer to one of the ends of elongated body 29 than its other end. Face seal portion 30 includes a sealing surface 33 for providing a seal with a surface 35 of valve seat 34 when pump assembly 10 is configured for filling of an implantable cylinder. Face seal portion 30 also includes chamfer 31 for providing a seal with flange 44 when pump assembly 10 is configured for deflation of an implantable cylinder. Surface 35 of valve seat 34 that contacts surface 33 of face seal portion 30 is preferably a generally smooth surface that allows for a fluid tight seal between surface 33 of face seal portion 30 and surface 35 of valve seat 34, when such sealing is desired. A spring 32 engages reservoir poppet 28 and biases reservoir poppet 28 toward valve seat 34.

Fluid passageway 24 further includes flange 44 configured generally as a ring-like portion within passageway 24 that preferably extends toward the center of passageway 24 around the inner perimeter of fluid passageway 24. Flange 44 is provided to reduce the inner diameter of passageway 24 by a sufficient amount so that the inner diameter in the area of flange 44 is smaller than the outer diameter of face seal portion 30. In this way, flange 44 can engage with chamfer 31 to hold reservoir poppet 28 against the bias of spring 32. Flange 44 preferably has sufficient strength to hold face seal portion 30 against the bias of spring 32, but also is flexible enough to allow movement of face seal portion 30 through or past flange 44 in either direction (i.e., to the right or left with respect to FIG. 5). Flange 44 may be annular and extend around the inner perimeter of passageway 24, as shown, or may instead have a different shape or configuration that can provide the function of engaging and disengaging sufficiently with face seal portion 30 in the manner described above. Further, flange 44 may be formed integrally with passageway 24 or may be formed separately and attached to the interior of passageway 24, such as with adhesives or the like. Spring 32 preferably has sufficient spring force to provide the desired amount of sealing between face seal portion 30 and valve seat 34 when face seal portion 30 is above flange 44 with respect to FIG. 6 (see FIG. 13, for example). Spring 32 should not be so strong, however, that it pushes reservoir poppet 28 past flange 44 toward valve seat 34 when it is instead desired for face seal portion 30 to be on the opposite side of flange 44.

Fluid passageway 24 also includes within its internal area a poppet valve seat 40 having sealing surface 41 adjacent to cylinder poppet 36. Cylinder poppet 36 includes face seal portion 37 that is preferably a ring-like protrusion that extends around the outer perimeter of cylinder poppet 36. Face seal portion 37 includes a sealing surface 39 for providing a seal with surface 41 of valve seat 40. Surface 41 of valve seat 40 that comes into contact with surface 39 of face seal portion 37 is preferably a generally smooth surface that allows for a fluid tight seal between surface 39 of face seal portion 37 and surface 41 of valve seat 40, when such sealing is desired.

Figure 13:
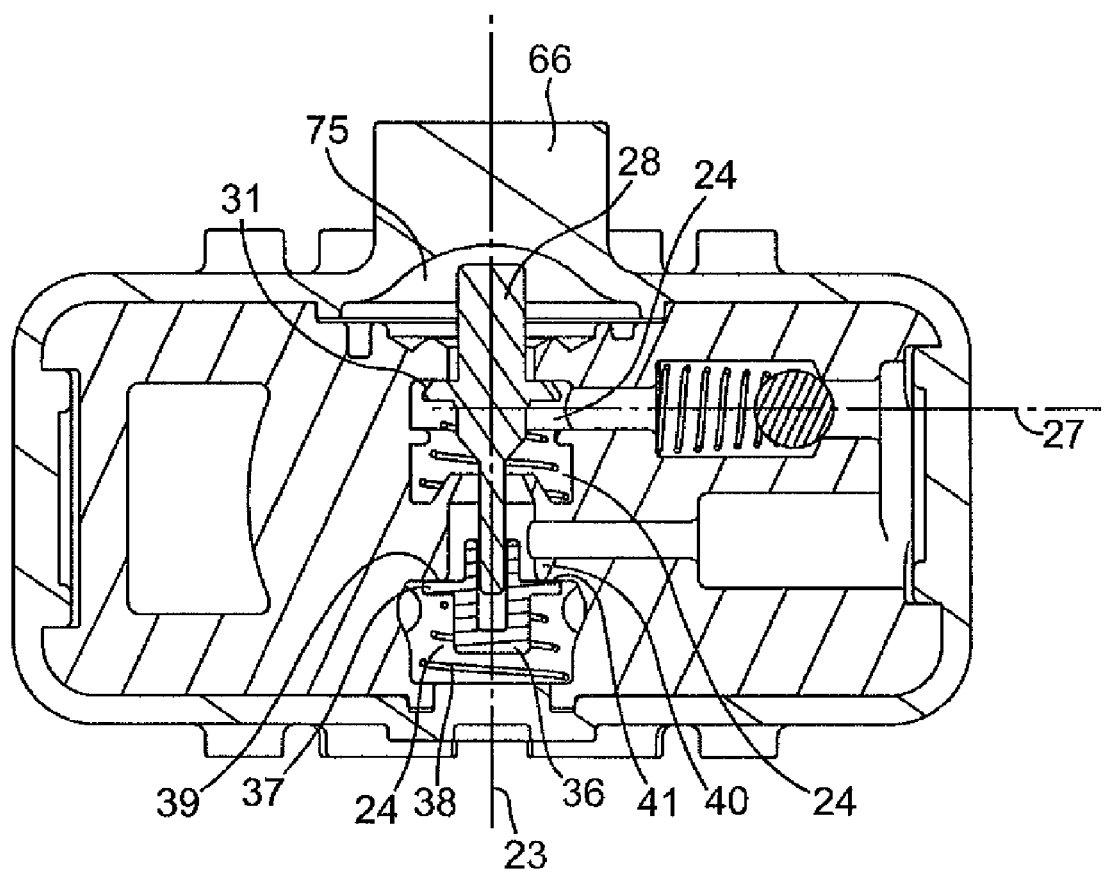
FIG. 13 is another cross-sectional view of the pump assembly illustrated in FIG. 6, with the internal components configured in a different operating condition of the pump.

In FIG. 13, pump assembly 10 is shown in a configuration where sealing surface 39 of poppet face seal portion 37 contacts sealing surface 41 of poppet valve seat 40 to provide a fluid tight seal. Poppet spring 38 engages cylinder poppet 36 and biases cylinder poppet 36 toward valve seat 40. Poppet spring 38 is preferably strong enough to provide a fluid tight seal between sealing surface 39 of poppet face seal portion 37 and sealing surface 41 of valve seat 40. Spring 38 is preferably not so strong that the cylinder poppet 36 is prevented from being moved back to its position shown in FIGS. 5 and 6. Such a movement of cylinder poppet 36 away from valve seat 40 allows fluid to pass from fluid passageway 24 into ports 20 and 21 during operation of pump assembly 10.

The internal area or portion of fluid passageway 24 further includes a lip seal 42 that extends generally from the area between valve seat 40 and flange 44. In one preferred embodiment, lip seal 42 may be generally conical in shape such that it tapers from a first cross-section in the pump body to a point or edge at its other end. This lip seal 42 is shown in cross-section in FIG. 6 as a finger-like portion that extends into fluid passageway 24. It is contemplated, however, that lip seal 42 has a different configuration or shape for sealing against the outside surface of reservoir poppet 28. Lip seal 42 is preferably configured so that it can contact the outer surface of reservoir poppet 28 and provide a fluid tight seal between lip seal 42 and reservoir poppet 28 when reservoir poppet 28 is positioned with face seal portion 30 out of contact with valve seat 34, and with chamfer 31 in contact with flange 44. Lip seal 42 is preferably further configured to allow smooth movement of reservoir poppet 28 into and out of contact with lip seal 42. However, lip seal 42 will be spaced from the outer surface of reservoir poppet 28 when the portion of reservoir poppet 28 that is adjacent to lip seal 42 is smaller in diameter than lip seal 42. This will occur, for example, when reservoir poppet 28 is moved so that face seal portion 30 is in contact with valve seat 34. In this mode, fluid would then be able to move through fluid passageway 24 and past lip seal 42.

As illustrated in FIG. 6, cylinder poppet 36 includes receiver 48 that is designed to slidingly engage with nose portion 50 of reservoir poppet 28. As shown, receiver 48 provides an opening or hole that can receive and engage with nose portion 50. Such engagement between nose portion 50 and receiver 48 helps to maintain coaxial alignment of reservoir poppet 28 and cylinder poppet 36 in pump body 12 and throughout the range of travel of reservoir poppet 28 and cylinder poppet 36. Nose portion 50 and reservoir poppet 28 can be designed in any manner that provides at least some overlapping sliding engagement between reservoir poppet 28 and cylinder poppet 36 for providing an aligning function between these components. When reservoir poppet 28 is moved away from valve seat 34 so that chamfer 31 is engaged with flange 44 against the bias of spring 32, nose portion 50 of reservoir poppet 28 can slide within and push against an inside end surface of receiver 48 of cylinder poppet 36 against the bias of poppet spring 38, thereby allowing for a certain fluid flow path. Thus, it is also preferable that poppet spring 38 and spring 32 are chosen to provide the desired ease of movement of components. That is, undue force should not be required to move the springs and poppets through the various operation modes of pump assembly 10. In particular, it is required for operation of pump assembly 10 that the sides of pump body 12 are compressible to thereby manipulate the position of reservoir poppet 28 and cylinder poppet 36 relative to each other and pump body 12. In order for this to be possible, it is preferable that reservoir poppet 28 is in sufficiently close proximity to the side of pump body 12 so that squeezing pump body 12 with a reasonable amount of force will move reservoir poppet 28 within pump body 12 into certain positions.

Pump body 12 further includes fluid bypass chamber 46 that is connected for fluid communication with fluid passageway 24 under certain operating conditions or modes of pump assembly 10. Fluid bypass chamber 46 includes ball check valve 54 having ball 56 and spring 58. Spring 58 biases ball 56 within chamber 46 along a check valve axis 27 toward ball valve seat 52, which is a portion or edges of chamber 46 that form a diameter that is smaller than the diameter of ball 56. In this way, a fluid tight seal may be formed between ball 56 and ball valve seat 52 when the system is in a state of equilibrium or when there is fluid pressure in chamber 64. This seal prevents the undesired movement of fluid through bypass chamber 46 except under certain operating conditions of pump assembly 10. As with the other springs used in pump assembly 10, spring 58 should be sufficiently strong to keep ball 56 in its normal or closed position against ball valve seat 52 under certain operating circumstances. However, spring 58 should also allow for a predetermined flow of fluid against the bias of spring 58 to move the ball 56 out of contact with ball valve seat 52 to allow fluid to flow through bypass chamber 46. As shown, fluid may move from fluid passageway 24 into bypass chamber 46 through a bypass input channel 62 during a deflation configuration of pump assembly 10.

When there is a sufficient pressure in combination with sufficient volume of pressurized fluid in chamber 46 to move ball 56 against the bias of spring 58, the fluid will be able to move freely from input channel 62 and through bypass chamber 46. Fluid may then exit bypass chamber 46 through bypass output channel 64 that provides a second fluid connection between bypass chamber 46 and fluid passageway 24. Bypass output channel 64 is positioned with respect to lip seal 42 so that certain operating conditions will provide a fluid path in which fluid passes by reservoir poppet 28 and enters transfer chamber 22. The valve style used in fluid bypass chamber 46 of FIG. 1 is shown as a ball check valve, but it could instead include any number of designs such as a "duck bill valve", flap, or the like, which react to pressurized fluid in generally the same manner as the ball check valve 54.

In order to provide a compact design, the check valve axis 27 as defined by bias direction of spring 58 is preferably provided at an angle greater than zero degrees (non-parallel) to the poppet valve axis 23 of reservoir poppet 28 and cylinder poppet 36. If the check valve axis 27 and poppet valve axis 23 are generally parallel, bypass input chamber 62 and bypass output chamber 64 would be spaced further apart than in configurations where the check valve axis 27 is at an angle to the poppet valve axis 23 in order to accommodate the check valve 54. This would have the effect of increasing width 25 of pump body 12. In the arrangement where the check valve axis 27 and poppet valve axis 23 are generally perpendicular, bypass input chamber 62 and bypass output chamber 64 are closer together such that the width 25 of pump body 12 can be at least slightly smaller.

The components of pump assembly 10 can be positioned in a configuration that provides an auto-inflation resistance mode. In this mode, the cylinders are in a deflated condition and spontaneous inflation of the cylinders will preferably be difficult or impossible due to the positions of the poppets, springs and chambers of pump assembly 10. No inflation of the cylinders can occur until pump bulb 14 is manipulated in a specified manner. In this mode, the fluid of the system will typically be contained within reservoir port 18, transfer chamber 22, and the reservoir (not shown), and this fluid cannot travel into ports 20 and 21 and the attached cylinders. In this mode, reservoir poppet 28 is being held against the bias of spring 32 by flange 44 within fluid passageway 24. Nose portion 50 of reservoir poppet 28 is engaged with the receiver 48 of cylinder poppet 36 in a way that pushes cylinder poppet 36 against the bias of poppet spring 38. Reservoir poppet 28 is thus positioned so that its outer surface is in contact with lip seal 42, thereby creating a fluid-tight seal between reservoir poppet 28 and lip seal 42.

In most cases, some portion of the fluid from the reservoir will move into port 18 and transfer chamber 22, particularly when the reservoir is under pressure. Any such pressurized fluid in transfer chamber 22 can move into fluid passageway 24 and move reservoir poppet 28 slightly toward cylinder poppet 36. This movement of reservoir poppet 28 allows fluid to flow from transfer chamber 22 through a gap between face seal portion 30 and reservoir poppet valve seat 34. This fluid will then enter internal chamber 16 through connecting channel 26. Movement of fluid into chamber 16 of pump bulb 14 will stop when the pressure has generally equalized between chamber 16 and the reservoir. The bias of spring 32 can then move face seal portion 30 back into contact with valve seat 34, thereby limiting or preventing further fluid flow into chamber 16.

Because lip seal 42 and reservoir poppet 28 form a fluid tight seal, as described above, no fluid can move past this seal toward ports 20 and 21 and connected cylinders. In addition, fluid attempting to move into fluid bypass chamber 46 through bypass output channel 64 will be prevented from moving past ball check valve 54 by the seal of ball 56 against ball valve seat 52. Thus, no fluid will be able to pass into fluid passageway 24 or ports 20 and 21 by this path. In this state of equilibrium, fluid will thus be held within the reservoir, connecting reservoir port 18, transfer chamber 22, annular channel 68, radial channels 70, 72, and 74, as well as chamber 16. When the pump is configured in this mode, there may be small amounts of residual fluid contained in the various portions of the pump assembly, and the cylinders will be partially or completely deflated or collapsed.

The components of pump assembly 10 can be positioned in a manner that provides an activation mode of pump assembly 10 for cylinder inflation. This is the mode in which the user activates pump assembly 10 to begin the process of cylinder inflation. To activate pump assembly 10, pump bulb 14 is squeezed or compressed by the user. This motion forces the fluid contained within pump chamber 16 through connecting channel 26 and into fluid passageway 24 under relatively high fluid pressure. This high pressure fluid forces chamfer 31 of face seal portion 30 of reservoir poppet 28 past flange 44, which flange is made of a material that is relatively flexible to allow face seal portion 30 to move past it, yet sufficiently strong to hold reservoir poppet 28 against the bias of spring 32. The bias of spring 32 will then push reservoir poppet 28 and face seal portion 30 against valve seat 34, thereby providing a fluid tight seal between face seal 30 and valve seat 34. Because the portion of reservoir poppet 28 adjacent lip seal 42 is now smaller in diameter than the internal opening provided by lip seal 42, lip seal 42 is not in contact with reservoir poppet 28 in this mode (i.e., a gap is created between reservoir poppet 28 and lip seal 42). Thus, fluid can move past lip seal 42 and toward cylinder poppet 36. In order for fluid to move past cylinder poppet 36 and into ports 20 and 21, however, the fluid pressure must be high enough to overcome the bias of poppet spring 38, which is now pushing cylinder poppet 36 in fluid tight contact with poppet valve seat 40. The amount and pressure of the fluid may or may not be sufficient to cause such a movement of cylinder poppet 36 in this pump activation mode.

Where the fluid pressure is sufficiently high to overcome the bias of poppet spring 38, fluid-tight contact between cylinder poppet 36 and poppet valve seat 40 can be broken, thereby providing a gap between sealing surface 39 of poppet face seal portion 37 and sealing surface 41 of valve seat 40. This may be referred to as the pumping mode of pump assembly 10. Fluid may then flow past lip seal 42 and cylinder poppet 36, and then into ports 20 and 21 and the attached inflatable cylinders. In particular, after a first volume of pressurized fluid from pump bulb is moved past cylinder poppet 36 and into the cylinders (e.g., as described above), the bias of poppet spring 38 will push cylinder poppet 36 back into contact with poppet valve seat 40 to stop flow so that pump bulb 14 can be refilled.

In the pump bulb filling mode, pump bulb 14 is pulling or drawing fluid from the reservoir and through the various chambers of the system. Pump bulb 14 is preferably selected from a material that is relatively elastic and easy for a user to compress, but should also have sufficient structural integrity that it tends to move back toward its original size or configuration when not subjected to external pressure. That is, when the user releases pump bulb 14, it should expand generally to its original shape and size, thereby providing a situation where pump bulb chamber 16 and fluid passageway 24 are placed under negative pressure. This negative pressure provided by the expansion of pump bulb 14 will draw fluid from the reservoir through reservoir port 18 and into chamber 16 of pump bulb 14. The negative pressure within pump bulb 14 and connected chambers can move reservoir poppet 28 in a way that breaks the seal between face seal portion 30 and valve seat 34. Fluid may then flow from the reservoir into annular channel 68, radial channel 70, 72, and 74, and transfer chamber 22, past face seal portion 30, and into fluid passageway 24. Any fluid under negative pressure within fluid passageway 24 will move into chamber 16 of pump bulb 14 until chamber 16 is full and/or there is no longer enough negative fluid pressure to keep face seal portion 30 from moving toward valve seat 34. Spring 32 then causes reservoir poppet 28 to reseat itself against valve seat 34. At this point, the user may then squeeze or compress pump bulb 14 to again move fluid from pump bulb 14 into ports 20 and 21 and inflatable cylinders, as described above.

Under certain conditions, when pump bulb 14 is pulling or drawing fluid from the reservoir and through the various chambers of the system, negative fluid pressure may cause reservoir poppet 28 to move in a way where a seal can be formed between face seal portion 30 and flange 44. If such seal is formed, a situation might exist in which the negative pressure in pump bulb 14 prevents reservoir poppet 28 from moving toward valve seat 34. This condition may prevent fluid from flowing from the reservoir to refill the pump bulb 14. If this occurs, some corrective action may be required such as may include at least some deflation of the cylinders before the inflation process can continue.

Figure 10:
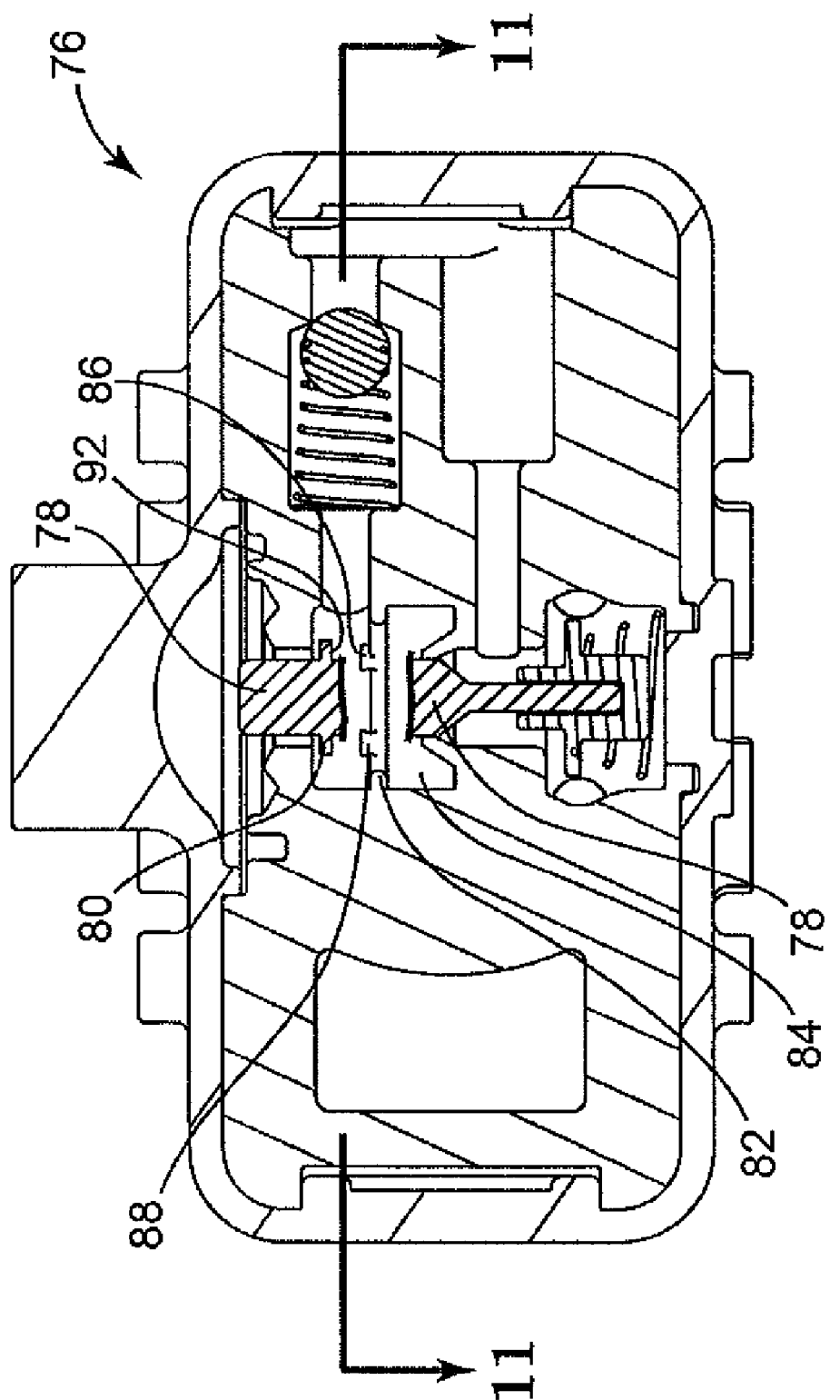
FIG. 10 is a cross-sectional view of another embodiment of a pump assembly of the invention.
Figure 11:
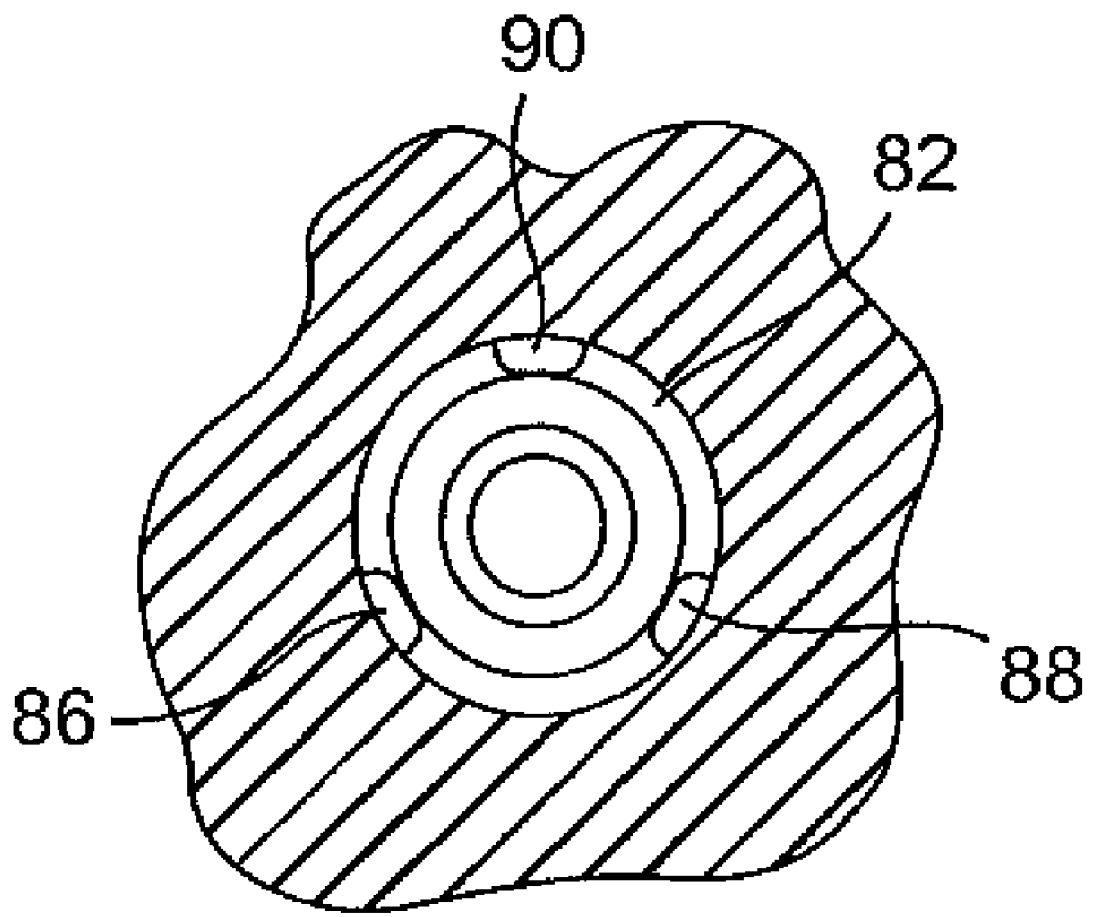
FIG. 11 is a cross-sectional view of the pump assembly of FIG. 10 taken along the line 11-11.

In order to provide a free path for fluid flow if reservoir poppet 28 and flange 44 come into contact with each other during pump bulb refilling, pump assembly 10 preferably includes a low flow fluid path such as a vent or controlled leak or the like that permits some fluid flow from one side of flange 44 to the other side in the event that face seal portion 30 is drawn into contact with flange 44. One configuration of such a fluid path is illustrated in FIGS. 10 and 11. In particular, FIG. 10 shows a cross-sectional view of pump assembly 76, which is preferably similar to pump assembly 10 of FIG. 1. FIG. 11 shows a cross-sectional view of pump assembly 76 taken along the line 11-11 of FIG. 10. Pump assembly 76 includes suction poppet 78 having face seal portion 80. Flange 82 is positioned within fluid passageway 84 and includes protrusions 86, 88, and 90. As shown, protrusions 86, 88, and 90 extend outwardly from flange 82 and are spaced apart around the circumference of flange 82. In this way, if surface 92 is drawn into contact with protrusions 86, 88, and 90, a gap is provided between flange 82 and face seal portion 80 that can allow for fluid flow through the gap. Such protrusions can be provided on flange 82, face seal portion 80, or both. This provides another fluid path between surface 92 and flange 82. Any bumps, ridges, grooves, openings, channels, or the like that function to allow fluid flow when surface 92 contacts flange 82 can be used. For example, a small opening(s) such as a hole or orifice can be provided in one or both of flange 82 and face seal portion 80.

The sequence of filling pump bulb 14 under negative pressure and forcing the fluid from pump bulb 14 under positive pressure may be repeated as many times as necessary to achieve the desired inflation of the cylinders and/or to empty the connected reservoir. Once inflated, the fluid within the cylinders and ports 20 and 21 is under relatively high pressure. While poppet spring 38 preferably has a sufficiently strong bias to keep cylinder poppet 36 pressed against poppet valve seat 40, the relatively high pressure fluid in the cylinders and connected chambers also pushes sealing surface 39 of face seal portion 37 of cylinder poppet 36 into contact with sealing surface 41 of valve seat 40, further strengthening this seal. This seal between cylinder poppet 36 and valve seat 40 is particularly important to keep the cylinders inflated (i.e., to prevent undesirable transfer of fluid from the cylinders into fluid passageway 24). Because the only path for fluid to move from ports 20 and 21 into fluid bypass chamber 46 is through fluid passageway 24, it is likewise not possible for fluid from the cylinders to move into fluid bypass chamber 46 without first breaking the seal between cylinder poppet 36 and its poppet valve seat 40.

When the user desires to deflate the cylinders, the walls of pump body 12 will be manually compressed in the general area of fluid passageway 24. In order to assist the user in finding the proper area for compression, the outer surface of pump body 12 may be provided with raised or otherwise detectable areas for easier determination of proper manipulation locations on the pump body 12. One example of such a detectable area is illustrated as a user pressure pad 66, which is a raised surface portion on the side of pump body 12 that would be detectable by the human fingers. A compressive force on pump body 12 at pressure pad 66 forces reservoir poppet 28 away from valve seat 34 by a sufficient distance that face seal portion 30 moves toward cylinder poppet 36 past flange 44. When the compressive force on pump body 12 is released, flange 44 then engages face seal portion 30 at chamfer 31 to hold reservoir poppet 28 in place against the bias of spring 32. This compression of pump body 12 simultaneously moves nose portion 50 of reservoir poppet 28 into contact with receiver 48 of cylinder poppet 36, which also breaks the seal between cylinder poppet 36 and poppet valve seat 40. Further, such pump body compression also causes reservoir poppet 28 to be in a position where lip seal 42 is in contact with reservoir poppet 28, which provides a fluid tight seal between these surfaces. Fluid from the cylinders and connecting ports 20 and 21 may then flow around cylinder poppet 36, past poppet valve seat 40, and into bypass input channel 62. Notably, a single compressive squeeze by the user is sufficient to put pump assembly 10 in this cylinder deflation mode. In other words, there is no need for the user to continue to hold pump body 12 in this compressive condition while the cylinder deflation is occurring.

Once the fluid enters bypass input channel 62, it moves directly into fluid bypass chamber 46, where sufficient fluid pressure can unseat ball 56 from ball valve seat 52 and allow fluid to move out of chamber 46 through bypass output channel 64 and into fluid passageway 24. The fluid can then move through annular channel 68, radial channels 70, 72, and 74, and then into transfer chamber 22 to port 18, and then into the reservoir. Fluid also flows into an open space 75 that extends into the general area of the pressure pad 66. Annular channel 68 and radial channels 70, 72, and 74 are preferably designed to allow fluid to flow from fluid passageway 24 to transfer chamber 22 when pressure pad 66 is being compressed to activate the deflation mode and space 75 is minimized or eliminated by compression of pad 66. In this way, fluid flow will not be interrupted if compression of pressure pad 66 is maintained.

Because the fluid within the cylinders before deflation is under relatively high pressure, an initial volume of pressurized fluid will move under pressure from ports 20 and 21 and into pump body 12 upon compression of pump body 12. After this initial volume has been transferred and the fluid has reached an equilibrium pressure, the cylinders may be manually compressed or manipulated to transfer the remainder of the fluid to the reservoir without the need to squeeze pad 66 or hold the pump, thereby completely deflating the cylinders. Pump assembly 10 is then configured again in its auto-inflation resistance mode, as described above.

Figure 12:
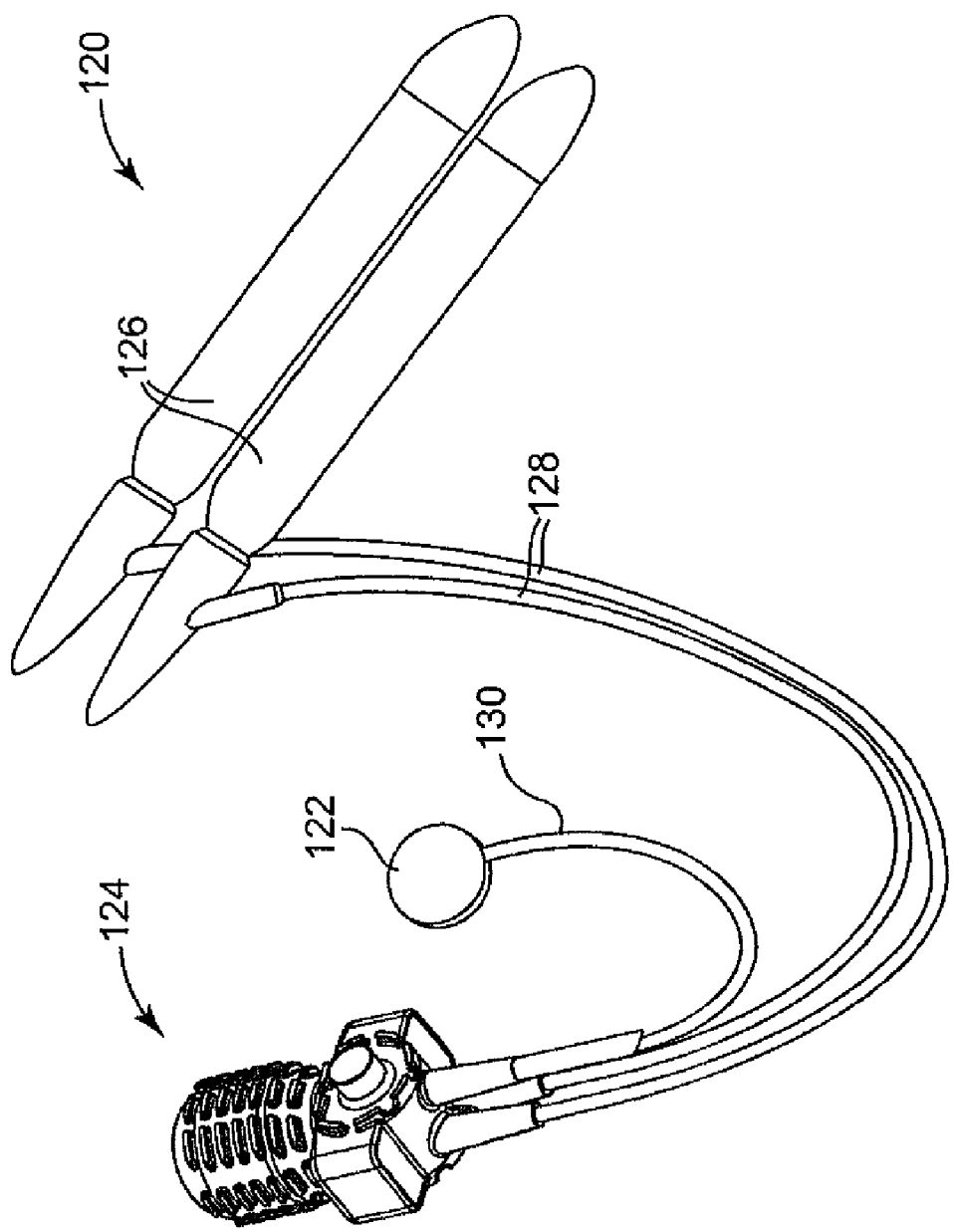
FIG. 12 illustrates a schematic perspective view of an implantable penile prosthesis device having a pump assembly of the type illustrated in FIGS. 1 through 11.

FIG. 12 illustrates an embodiment of an implantable penile prosthesis system 120 of the invention, which includes a pump of the type illustrated in FIGS. 1 through 11, reservoir 122 that is separate from pump assembly 124, and cylinders 126. In general, this system 120 utilizes pump assembly 124 and reservoir 122 to inflate cylinders 126, with connecting tubing attached between pump assembly 124 and both reservoir 122 and cylinders 126. Pump assembly 124 can also be used to deflate the cylinders, as described above. Reservoir 122 is preferably constructed from a thick, high durometer elastomeric material, such as silicone and is specifically sized to hold a certain volume of fluid that corresponds to at least the volume difference desired to expand the cylinders 126.

As shown, two tubes 128 extend from pump assembly 124, each of which connects to one of cylinders 126. A single tube 130 extends from reservoir 122 for connection to pump 124. It is contemplated, however, that the number of tubes and the branching of tubes can differ from this arrangement, depending on the design of the pump and other components. As described above relative to pump assembly 10, the body of pump assembly 124 can be squeezed generally along its longitudinal axis in order to deflate cylinders 126, which thereby opens certain valves within the pump and allows pressurized fluid from the cylinders to move through the pump and enter the reservoir. Inflation of the cylinders can be accomplished by first squeezing the pump bulb to activate pump assembly 124, then squeezing the pump bulb repeatedly until the desired cylinder inflation is achieved.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A pump for transferring fluid between a fluid reservoir and at least one inflatable penile prosthesis, the pump comprising:
   a pump housing having a fluid passageway;
   first and second fluid ports in fluid communication with the fluid passageway and operatively connectable to a fluid reservoir and at least one inflatable penile prosthesis, respectively;
   a pump bulb in fluid communication with the fluid passageway that can be operated to transfer fluid between the first and second fluid ports through the fluid passageway;
   first and second poppets positioned within the fluid passageway, aligned along a valve axis, and biased toward first and second valve seats within the fluid passageway, respectively, wherein the first poppet comprises an end slidingly engaged with the second poppet and an extending portion extending away from a body portion of the first poppet;
   a flange spaced from the first valve seat within the fluid passageway and extending from a surface of the fluid passageway toward an interior area of the fluid passageway;
   a first fluid path between the extending portion of the first poppet and the flange when the extending portion of the first poppet is in contact with the flange, wherein the first fluid path can allow fluid to pass from one side of the flange to the other; and
   a second fluid path providing fluid communication between the fluid passageway and a fluid bypass chamber when the extending portion of the first poppet is in contact with the first valve seat;
   wherein the fluid bypass chamber is fluidly connected by a bypass input channel to the fluid passageway at a first location and fluidly connected by a bypass output channel to the fluid passageway at a second location.

* * * * *